(12) United States Patent
Gilby et al.

(10) Patent No.: US 6,997,031 B2
(45) Date of Patent: Feb. 14, 2006

(54) FRACTION COLLECTOR FOR COMPOSITION ANALYSIS

(75) Inventors: Anthony Gilby, Foxborough, MA (US); Andrew Simon Craze, Thame (GB)

(73) Assignee: Waters Corporation, Milford, MA (US)

( * ) Notice: Subject to any disclaimer, the term of this patent is extended or adjusted under 35 U.S.C. 154(b) by 0 days.

(21) Appl. No.: 10/427,324

(22) Filed: May 1, 2003

(65) Prior Publication Data

US 2004/0216510 A1    Nov. 4, 2004

(51) Int. Cl.
*G01N 30/82* (2006.01)
(52) U.S. Cl. ........................ 73/1.02; 702/100
(58) Field of Classification Search ................ 73/1.02, 73/1.42, 1.45, 61.57; 702/89, 100
See application file for complete search history.

(56) References Cited

U.S. PATENT DOCUMENTS

| | | | | |
|---|---|---|---|---|
| 3,516,577 | A | * | 6/1970 | Pitt .............................. 222/309 |
| 4,971,915 | A | * | 11/1990 | Schwartz et al. ............ 436/139 |
| 5,668,735 | A | * | 9/1997 | Dominguez et al. ..... 702/100 X |
| 5,987,959 | A | * | 11/1999 | Klee et al. .................... 73/1.02 |
| 6,106,710 | A | * | 8/2000 | Fischer et al. ............ 210/198.2 |
| 6,406,633 | B1 | * | 6/2002 | Fischer et al. .......... 73/61.57 X |
| 6,660,149 | B1 | | 12/2003 | Karger et al. ................ 204/601 |
| 6,691,053 | B2 | * | 2/2004 | Quimby et al. ................ 702/89 |
| 6,767,467 | B2 | | 7/2004 | Fischer et al. ............... 210/659 |

FOREIGN PATENT DOCUMENTS

| | | |
|---|---|---|
| EP | 0 274 847 B1 | 3/1993 |
| EP | 0 692 713 A1 | 1/1996 |
| EP | 0 749 972 A1 | 12/1996 |
| EP | 0 639 098 B1 | 8/1998 |
| EP | 0 639 099 B1 | 8/1998 |
| EP | 0 662 013 B1 | 5/1999 |
| EP | 0 724 901 B1 | 9/2002 |
| EP | 0 835 446 B1 | 4/2003 |
| JP | 06-102246 | 4/1994 |
| JP | 11-258224 | 9/1999 |
| WO | WO 97/00877 | 1/1997 |
| WO | WO 99/05319 | 2/1999 |
| WO | WO 99/22228 | 5/1999 |

OTHER PUBLICATIONS

A. Baj et al., "Qualitative and Quantitative Evaluation of Vaccinium Myrtillus Anthocyanins By High-Resolution Gas Chromatography and High-Performance Liquid Chromatography", *Journal of Chromatography*, vol. 279, pps: 365-372, 1983, month not given.

W. Christie, "Separation of Molecular Species of Triacylglycerols by High-Performance Liquid Chromatography with a Silver Ion Column", *Journal of Chromatography;* vol. 454; pps: 273-284; 1988, month not given.

(Continued)

*Primary Examiner*—Thomas P. Noland
(74) *Attorney, Agent, or Firm*—Brian L. Michaelis; Brown Rudnick Berlack Israels LLP

(57) ABSTRACT

A method and apparatus for controlling fraction collection in an eluent stream flowing from an LC column. A triggering detector recognizes the presence of a target substance according to characteristics of chromatographic peaks in the eluent stream and initiates a delay timer to trigger the fraction collector. A waste stream detector is disposed at any distance from the fraction collector to detect peaks in the waste stream flowing from a fraction collector. The signature of fraction collector actuation is seen by the waste stream detector, permitting the delay time to be adjusted for optimal collection of the target compound. The presence or absence of a peak or the characteristics of a remnant peak detected by the waste stream detector are used to confirm that the target component of the eluent stream was collected as intended by the fraction collector.

11 Claims, 7 Drawing Sheets

OTHER PUBLICATIONS

Jos F. H. M. Brouwers et al., "Rapid separation and identification of phosphatidylethanolamine molecular species", *Journal of Lipid Research,* vol. 40, pps: 164-169, 1999, month not given.

William W. Christie, et al., "Separation of Picolinyl Ester Derivatives of Fatty Acids by High-Performance Liquid Chromatography for Identification by Mass Spectrometry", Journal of Chromatography, vol. 392, pps. 259-265, 1987, month not given.

Ewa Dolecka, et al., "Variable Splitter for Regulation of the Solvent Evaporation Rate in the Coupling of Liquid Chromatography with Gas Chromatography," *Journal of High Resolution Chromatography,* vol. 13, pps. 405-409, Jun. 1990.

J. N. Driscoll, et al., "Trace Analysis of Organic Compounds by High-Performance Liquid Chromatography with Photoionization Detection", *Journal of Chromatography,* vol. 302, pps. 43-50, 1984, month not given.

Timothy G. Heath, et al., "Reversed-phase capillary high-performance liquid chromatography with on-line UV, fluorescence and electrospray ionization mass spectrometric detection in the analysis of peptides and proteins", *Journal of Chromatography* vol. 638, pps. 9-19, 1993, month not given.

Tony Herlt, "A Facile Separation of Nonactin and its Homologues", *J. Liq. Chrom. & Rel. Technol.,* vol. 20(8), pps. 1295-1300, 1997, month not given.

Masanori Hori, et al., "Molecular Species Analysis of Polyunsaturated Fish Triacylglycerol by High-Performance Liquid Chromatography/Fast Atom Bombardment Mass Spectrometry", *Analytical Sciences,* vol. 10, pps. 719-724, Oct. 1994.

Fong-Fu Hsu, et al., "Preparative high-performance liquid chromatography using detection by thermospray mass spectrometry", *Journal of Chromatography,* vol. 478, pps. 429-432, 1989, month not given.

Sheri L. Jordan, et al., "Identification of an anti-bacterial agent in toothpaste via liquid chromatography—Fourier transform infrared spectrometry mobile phase elimination", *Journal of Chromatography A,* vol. 755, pps. 211-218, 1996, month not given.

P. Juanéda, et al., "Separation and Quantification of Heart and Liver Phospholipid Classes by High-Performance Liquid Chromatography Using a New Light Scattering Detector", *LIPIDS,* vol. 25, pps. 756-759, 1990, month not given.

Jeffrey P. Kiplinger, et al., "Structure-controlled Automated Purification of Parallel Synthesis Products in Drug Discovery", *Rapid Commun. Mass Spectrom,* vol. 12, pps. 658-664, 1998, month not given.

P. Kokkonen, et al., "Separation and Identification of Intact Glucosinolates Using Direct Coupling of High-performance Liquid Chromatography with Frit to Fast-atom Bombardment Mass Spectrometry", *Rapid Communications in Mass Spectrometry,* vol. 3, No. 4, pps. 102-106, 1989, month not given.

Mihály Kotrebai, et al., "Identification of the principal selenium compounds in selenium-enriched natural sample extracts by ion-pair liquid chromatography with inductively coupled plasma- and electrospray ionization-mass spectrometric detection", *Anal. Commun.,* vol. 36, pps. 249-252, 1999, month not given.

Zhaoyang Li, et al., "A subnanogram API LC/MS/MS quantitation method for depsipeptide FR901228 and its preclinical pharmacokinetics", *J. Pharm. Biomed. Anal,* vol. 22, pps. 33-44, 2000, month not given.

Jinping Liu, et al., "Miniaturized HPLC and ionspray mass spectrometry applied to the analysis of Paclitaxel and taxanes", *Journal of Pharmaceutical and Biomedical Analysis,* vol. 15, pps. 1729-1739, 1997, month not given.

Arjan J. H. Louter, et al., "On-line Solid-Phase Extraction-Thermal Desorption-Gas Chromatography with Ion Trap Detection Tandem Mass Spectrometry for the Analysis of Microcontaminants in Water", *J. High Resol. Chromatogr.,* vol. 19, pps. 679-685, Dec. 1996.

Eric D. Lund, et al., "A stream splitter for liquid chromatography", *J. Chromatog,* vol. 31, pps. 549-550, 1967, month not given.

F. A. Maris, et al., "On-line Trace Enrichment for Improved Sensitivity in Liquid Chromatography with Direct Liquid Introduction Mass Spectrometric Detection", *Journal of Chromatography,* vol. 323, pps. 113-120, 1985, month not given.

B. Pacciarelli, et al., "GC Column Effluent Splitter for Problematic Solvents Introduced in Large Volumes: Determination of Di-(2-ethylhexyl) Phthalate in Triglyceride Matrices as an Application", *Journal of High Resolution Chromatography & Chromatography Communications,* vol. 11, pps. 135-139, Jan. 1988.

Thomas V. Raglione, et al., "Liquid Chromatography-Gas Chromatography Interfacing Using Microbore High-Performance Liquid Chromatography with a Bundled Capillary Stream Splitter", *Analytical Chemistry,* vol. 58, No. 13, pps. 2680-2683, Nov. 1986.

Thomas V. Raglione, et al., "On-line Microbore High-Performance Liquid Chromatography-Capillary Gas Chromatography-Mass Spectrometry", *Journal of Chromatography,* vol. 409, pps. 205-212, 1987, month not given.

Herbert S. Rosenkranz, et al., "A Study on the Absorption of Nucleic Acids by Charcoal", *Journal of Chromatography,* vol. 30, pps. 549-555, 1967, month not given.

Dr. Ashley B. Sage, "High Throughput Characterisation & Purification of Combinatorial Synthetic Arrays by LC-UV-MS", Micromass UK Ltd, UK., 12 pps., by Feb. 2005.

Urban Skogsberg, et al., "Liquid chromatography-electrospray mass spectrometry method to separate and detect N-*tert.*- butoxycarbonyl peptides", *J. Chromatogr. A.,* vol. 808, pps. 253-256, 1998, month not given.

F. Valero, et al., "Biomass Estimation Using On-Line Glucose Monitoring by Flow Injection Analysis", *Applied Biochemistry and Biotechnology,* vol. 24/25, pps. 591-602, 1990, month not given.

F. Valero, et al., "On-line Fermentation Monitoring Using Flow Injection Analysis", *Biotechnology and Bioengineering,* vol. 36, pps. 647-651, 1990, month not given.

R. B. van Breemen et al., "Continuous-Flow Fast Atom Bombardment Mass Spectrometry of Oligonucleotides", *Am Soc. Mass Spectrom,* vol. 2, pps. 157-163, 1991, month not given.

"FractionLynx: MassLynx User Guide", Micromass, 43 pp., 1998, month not given.

"FractionLynx-*Pharma*™ the intelligent solution for selective autopurification", Micromass, Version 3.0, 35 pps., Dec. 1996.

Waters Corporation, "Waters® Auto-purification Systems Featuring FractionLynx™ Software", 6 pps., Jul., 1999.

Adsumo, New Products, 3 pps., 1998, mont not given.

"FractionLynx Users Guide", Micromass, Version 3.3, pps. Cover-ii and 37-38, Sep. 26, 1999.

* cited by examiner

FRACTION COLLECTOR FOR COMPOSITION ANALYSIS

FIELD OF THE INVENTION

This invention relates to a fluid system and particularly to fraction collection in a liquid chromatography ("LC") eluent stream.

BACKGROUND OF THE INVENTION

Liquid chromatography is commonly used for analyzing the composition of chemical compounds whereby solutions containing the compounds to be analyzed are forced under pressure through a liquid chromatography (LC) column. The LC column is specifically constructed to interact with the pressurized solution and affect the fluid flow rate in a way that is characteristic of the composition of chemicals in the solution. Components are thereby separated in the solution according to their chemical composition and corresponding flow rate. Eluent from the LC column is typically in a highly diluted liquid phase. Separated components are manifested as "chromatographic peaks" on detector apparatus.

In liquid chromatography analysis, the choice of an appropriate separation strategy, including the combined implementation of hardware, software, and chemistry, results in the separation of an injected sample into separate components, which elute from the column in reasonably distinct zones or "bands". As these bands pass through a detector, a detector output, usually in the form of an electrical signal, is produced. The pattern of analyte concentration within the eluting bands, which can be represented by means of a time-varying electrical signal, gives rise to the nomenclature "chromatographic peak" (or "peak"). Peaks may be characterized with respect to their "retention time," which is the time at which the center of the band transits a detector. In many applications, the retention time of a peak is used to infer the identity of the eluting analyte based upon related analyses with standards and calibrants. The retention time for a peak is strongly influenced by the mobile phase composition of the analyte and by the accumulated volume of mobile phase which has passed through the LC column.

It is often desirable to separate and collect specific component(s) from the HPLC separation of a complex mixture for further testing and evaluation. For example, samples of a pure component may be needed to evaluate the biological activity or other properties of a candidate drug molecule.

Conventional methods for physically collecting a purified sample from an eluent stream employ a fraction collector which is capable of diverting a portion or "fraction" of the stream into a collection vessel at a specified time. The specified time for opening the fraction collector ideally coincides with the arrival at the fraction collector of concentrated components of the eluent stream.

As is known in the art, timing of a fraction collector in an LC eluent stream can be controlled by installing a triggering detector which initiates a timer upon detection of a particular component concentration (peak). The fraction collector is triggered after a delay time elapses.

Any detector which senses a peak before it reaches the fraction collector can be used to trigger fraction collection. UV detectors are commonly used as triggering detectors in UV-directed purification or fraction collection systems. Mass spectrometers are commonly used as triggering detectors in mass-directed purification or fraction collection systems. These detectors can recognize a signature peak representing the presence of particular components and trigger the fraction collector to collect only desired components from the eluent stream. The triggering detector can be installed upstream of a fraction collector if it is a non-destructive detector such as a UV detector. However, the triggering detector is not necessarily installed directly upstream of a fraction collector. It can also be installed in one branch of a split flow wherein the other branch of the split flow is directed to the fraction collector. For example, if a destructive detector such as a mass spectrometer is used as a triggering detector, it must be installed in a separate branch of the eluent stream.

The delay time is the time between the appearance of a peak at the triggering detector and the arrival of the peak at the fraction collector. This time depends on the flow rate and fluid volume in the relevant connecting tubing. The delay time of an eluent stream can be determined by injecting a known calibrant such as a visible dye at an upstream location and recording the elapsed time between its detection by the triggering detector and its arrival at the fraction collector. One drawback of this calibration method is that the special calibrant dye must be injected whenever it is desired to check that the correct delay time is being used. For example, a change in flow rate for any reason will result in a change in delay time, which could go unnoticed.

Mass spectrometers are commonly used to analyze the composition of an eluent stream. U.S. Pat. No. 6,406,633 to Fischer et al. ("Fischer '633") and U.S. Pat. No. 6,106,710 to Fischer et al. ("Fischer '710") disclose a fraction collection system which directs a portion of an eluent stream from a liquid chromatography column to a mass spectrometer, and detects a desired component (peak) with the mass spectrometer. The apparatus of the Fischer disclosures is shown diagrammatically in FIG. 1. The mass spectrometer 52 triggers a delay timer for controlling the actuation of a fraction collector 54 in a separate branch of the stream. The eluent stream flows from a liquid chromatography column 51 to a splitter 57 which divides the eluent stream and directs one branch to a mass spectrometer 52 and another branch to a fraction collector 54. Even though the mass spectrometer 52 disclosed in Fischer '633 and Fischer '710 is disposed in a separate stream branch 53 rather than directly upstream of the fraction collector 54, the mass spectrometer 54 can be used to time the opening of the fraction collector 54 if the flow rates in each branch of the stream are related in a predictable way, and the peak is detected by the mass spectrometer before it reaches the fraction collector. A downstream detector 55 is disposed near the fraction collector 54. Detection of a peak at the downstream detector 55 allows the flow rate of the peak to be determined by measuring the elapsed time between detection of a sample upstream and its arrival at a downstream point near the fraction collector. The downstream detector 55 described in Fischer '633 and Fischer '710 is a non-destructive detector such as a UV detector.

To effect timing of the fraction collector 54 Fischer '633 discloses a delay time determined empirically by the injection of a calibrant in the eluent stream and timing the arrival of the calibrant at the mass spectrometer 52 in one branch of the stream. The arrival of the calibrant at downstream detector 55 proximate to fraction collector 54 in a separate branch of the stream is also timed. The delay between arrival of the calibrant at the mass spectrometer 52 and arrival of the calibrant at the downstream detector 55 provides flow rate information that can be used to time the opening of the fraction collector after a sample being analyzed is detected in the mass spectrometer.

Each of the various implementations described in Fischer '633 and Fischer '710 involves the use of a destructive detector such as a mass spectrometer to identify the presence of a substance in an eluent stream. The use of a destructive detector requires splitting the eluent stream into an analyzed stream flowing to the destructive detector and a collection stream flowing to the fraction collector. Fischer '633 and Fischer '710 also disclose various implementations of a third detector upstream from the fraction collector to better characterize the flow in each branch of the eluent stream in order to more accurately time the opening and closing of the fraction collector. The third detector is described in Fischer '633 and Fischer '710 as a non-destructive detector such as a UV detector.

The various implementations described in Fischer '633 and Fischer '710 require placement of a non-destructive detector near the fraction collector. Such placement is disadvantageous for use because typical fraction collectors use long robotic arms to dispense into collection vessels. If a detector must be located near a fraction collector dispensing head, only detectors suitable for mounting on a robotic arm can be used. This precludes use of standard HPLC detectors, for example a tunable UV detector, which can be used to detect a variety of components being separated, but are not suitable for mounting on a robotic arm.

No information regarding the accuracy of the fraction collector timing signal is provided by any apparatus described in Fischer '633 or Fischer '710. Furthermore, the various apparatus described in Fischer '633 and Fischer '710 do not provide confirmation that a desired component was successfully collected by a fraction collector. The delay time in Fisher '633 is determined using a calibrant. It is assumed to remain unchanged during sample collection, until such time as calibration is repeated.

Each of the various fraction collection methods described in Fischer '633 requires the use of a calibrant which is injected into the eluent stream for calibrating the delay period before the fraction collector is actuated. Persons skilled in the art will recognize that any calibrant may have different flow characteristics than the substance being analyzed. For example, a change in flow rate or split ratio could occur after calibration is performed. The calibrated delay period therefore may include errors that result in non-optimal collection of a desired substance at the fraction collector. Even small errors in timing can cause a fraction collector to miss much or all of a target substance.

None of the methods and apparatus heretofore known for controlling fraction collector timing in LC systems include a means to confirm the successful collection of a desired component in the eluent stream.

SUMMARY OF THE INVENTION

The present invention provides a method and apparatus for controlling fraction collection in an eluent stream flowing from an LC column. A triggering detector recognizes the presence of a target substance above a predetermined threshold level according to characteristics of chromatographic peaks in the eluent stream. A waste stream detector is disposed to detect peaks in the waste stream flowing from a fraction collector. Presence or absence of a peak in the waste stream above a predetermined threshold level indicates whether the peak was properly collected by the fraction collector. Characteristics of peaks detected by the waste stream detector are used to confirm that the target component of the eluent stream was actually collected by the fraction collector and to calibrate the timing of the fraction collector for optimal collection of the target component. Timing calibration depends on recognizing a fraction collector event, opening or closing, in the waste stream detector's signature of a peak. The timing calibration can be automated. There is no requirement for the waste stream detector to be placed close to the fraction collector. The waste stream can be led to any detector located in the purification system package.

An illustrative embodiment of the invention provides a method for collecting a sample component from an eluent stream out of a liquid chromatography (LC) column. The eluent stream is directed to a fraction collector for diversion of a specific portion or fraction of the stream to a collection vessel or alternate path for further analysis, separation or evaluation of the fraction. A waste stream carries the remainder of the eluent stream away from the fraction collector. The waste stream ceases to flow while the fraction collector is actuated. Characteristics of chromatographic peaks from the target sample component are detected in the waste stream. A calibrated delay time for actuating the fraction collector is computed according to the characteristics of peaks detected in the waste stream. The fraction collector timing is adjusted to effect optimum fraction collection.

The target component is first detected by a triggering detector before it reaches the fraction collector in the eluent stream. The fraction collector is actuated when an estimated delay time has elapsed after detection of a desired sample by the triggering detector. Some portions of the sample component are detected at the waste stream detector. The delay time used to open the fraction collector is tuned by evaluating the shape of chromatographic peaks that are detected in the waste stream and adjusting the delay time in response to characteristics of the peaks.

Non-destructive optical detectors such as UV detectors are particularly suitable for use as waste stream detectors in the various illustrative embodiments of the invention. The chromatograms output by UV detectors are tuned to a wavelength appropriate for detecting a desired peak. UV detectors are also particularly well suited for use as triggering detectors according to the present invention.

In another illustrative embodiment of the invention, a splitter is disposed upstream of the fraction collector and diverts a portion of the stream to a destructive detector such as a mass spectrometer. A delay timer for actuating the fraction collector can be initiated upon the detection of a desired peak by the mass spectrometer. Detection of peaks by the mass spectrometer can be used in the same manner as the triggering detector described hereinbefore if the flow path of the mass spectrometer is shorter (temporarily) than the flow path of the fraction collector so that a portion of the desired component reaches the mass spectrometer before a corresponding portion of the desired component reaches the fraction collector. Only about $1/1,000$ of the flow is directed to the mass spectrometer, and as a practical matter, a make-up pump is used to dilute the sample and speed it to the mass spectrometer. The high concentration of sample in the preparative stream is too high to inject directly into the electrospray interface of a mass spectrometer.

The present invention can also be implemented using a non-destructive triggering detector disposed upstream of a splitter. The splitter directs a branch of the eluent stream to any type of analysis equipment such as a mass spectrometer. The splitter directs a separate branch of the eluent stream to the fraction collector. Either the non-destructive triggering detector or the mass spectrometer can be used to detect the presence of a desired peak and initiate the delay timer to operate the fraction collector. Alternatively, a non-destructive detector can be located downstream of the splitter in either the stream branch directed to the destructive detector or in the stream branch directed to the fraction collector.

Any detector can be used as the waste line detector. In place of the UV detector discussed above, any non-destructive or destructive detector can be used. In particular when a mass spectrometer is employed as the triggering detector, a portion of the waste stream can be analyzed by multiplexing into a second analytical channel of the same mass spectrometer.

In each of the illustrative embodiments, a waste stream detector provides information used to adjust the timing of the fraction collector. For example, a full peak detected in the waste stream indicates that a target component was not collected by the fraction collector. Contrarily, a peak detected in a triggering detector but not in the waste stream, indicates that the fraction was collected properly at the fraction collector. Characteristics such as the width of a peak in the waste stream can be compared to similar characteristics of an upstream peak. A substantial match of such characteristics indicates that substantially the entire volume of a peak was missed by the fraction collector. A partial match between such characteristics indicates that only a portion of the peak was collected by the fraction collector. The particular differences between the shape of the peak at the waste stream detector with and without the fraction collector opening can be used to determine a precise actuation time adjustment that enables collection of the optimal volume of a target sample by the fraction collector.

In at least one illustrative embodiment, the delay period between the upstream detection of a target sample and the actuation of a fraction collector is adjusted during a setup operation. The fraction collector timing is verified and if necessary adjusted according to characteristics of peaks detected in the waste stream, periodically or each time the fraction collector is actuated.

In another illustrative embodiment, a calibrant component having properties detectable by both the triggering detector and the waste stream detector is injected upstream of the triggering detector during a setup process. The fraction collector can be timed to partially collect the calibrant peak. Characteristics of calibrant peaks detected in the waste stream can be used to calibrate the timing of the fraction collector.

The present invention overcomes the disadvantages of previously known methods by confirming the collection of a target sample in an eluent stream of a liquid chromatography (LC) column. The present invention further overcomes disadvantages of the prior art by optimizing the timing of a fraction collector to minimize the loss of target sample components. Timing information determined using data from the waste stream detector in the present invention allows continuous recalibration of the fraction collector timing.

The waste stream detector according to the present invention is not necessarily installed near the fraction collector or on the fraction collector dispensing arm, which makes large and rapid motions. Rather, the waste stream detector can be installed remotely from the fraction collector dispensing arm. This allows standard HPLC detectors to be used which operate on any separated peak, and do not require the prior art recourse to a calibrant dye. In addition, such placement overcomes many disadvantages of the prior art by facilitating use of parallel fraction collector dispensing heads with a single multiplexed waste stream detector. Such placement also allows the use of a standard UV detector having tunable wavelengths to detect a variety of compounds being separated. Placement of a detector in the waste stream according to the present invention also allows the use of a single multi-channel detector for both triggering detector and waste stream detector.

As examples, a single UV detector with 8 parallel flow-cells could be used for the triggering detectors as well as the waste line detectors for a 4-channel purification system. Similarly, an 8-way multiplexed mass spectrometer could be used to provide four independent triggering channels plus analysis of the four waste lines. In each case the delay timing of the four independent fraction collectors can be determined according to the invention.

The various embodiments of the present invention also provide advantages over previously known fraction collector techniques by eliminating the need to place a detector at or near the fraction collector, or to inject a calibrant component into the eluent stream. The present invention also eliminates fraction collector timing errors introduced by reliance in the prior art on flow characteristics of a calibrant that may be different from flow characteristics of a desired component at a later time in the eluent stream.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

The present invention will be described in detail with respect to chromatographic applications with the understanding that embodiments of the present invention are directed to industrial and process control applications as well.

Figure 1:
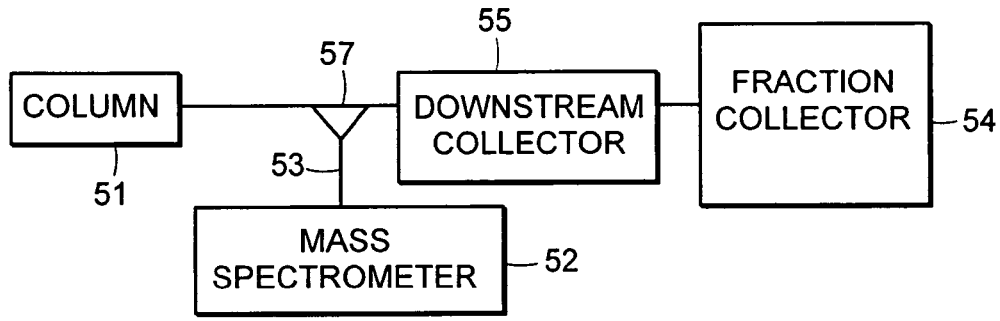
FIG. 1 is a diagrammatic representation of a system flow path including a downstream detector proximate to a fraction collector in a liquid chromatography eluent stream as known in the prior art.
Figure 2:
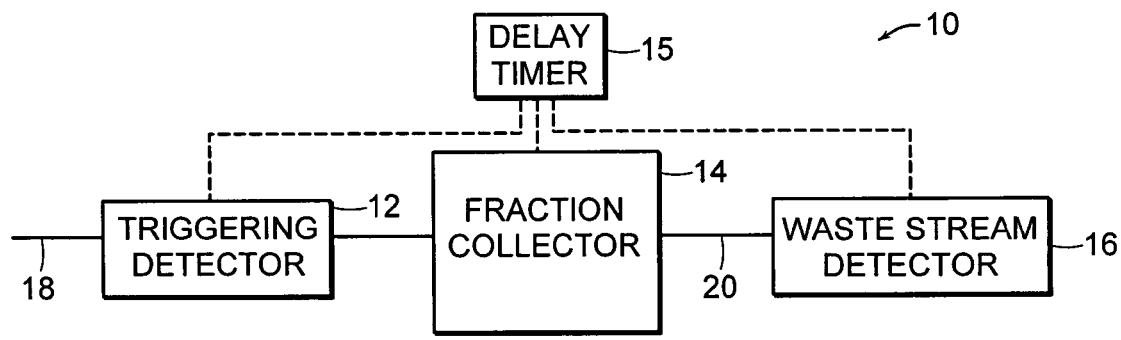
FIG. 2 is a diagrammatic representation of a system flow path including a triggering detector and a waste stream detector according to an illustrative embodiment of the present invention.

Referring to FIG. 2, a system flow path 10 according to an illustrative embodiment of the invention is shown diagrammatically. The system flow path 10 includes a triggering detector 12, a fraction collector 14 and a waste stream detector 16 arranged in series. A delay timer 15 is configured to introduce timed signals for actuating (opening and closing) the fraction collector 14. An eluent stream 18 from a liquid chromatography column (LC Column) (not shown) flows through the triggering detector 12 and continues on to the fraction collector 14. The fraction collector 14 is triggered by the delay timer 15 at an appropriate time to divert and collect or identify a particular component of the eluent stream 18. The portions of the eluent stream 18 that are not diverted by the fraction collector 14 continue along the flow path 10 into a waste stream 20. The waste stream 20 flows through the waste stream detector 16. The function of delay timer 15 may be provided by the chromatography management system software.

The eluent stream 18 includes a series of separated sample components in solution. Particular components are identifiable by the triggering detector 12 and the waste stream detector 16 as chromatographic peaks in the detector response. A chromatographic peak indicating the presence of a desired component in the eluent stream 18 at the triggering detector 12 initiates the fraction collector delay timer 15. The desired peak arrives at the fraction collector after a time delay that depends on the internal volume of tubing connecting the triggering detector to the fraction collector and on the flow rate of the component in the eluent stream. The fraction collector is opened when the time delay elapses and closes after a second delay. The second delay can be predetermined or determined by touch-down of the trailing edge of the peak at the triggering detector 12. The waste stream detector 16 detects the remnant peak in the eluent stream. The shape and timing of the remnant peak provide information to establish the optimal timing of fraction collection and provide an ongoing monitor to determine whether the desired fractions have been collected. The waste stream detector provides a signal which can automatically fine-tune the delay time between detection of a peak by the triggering detector 12 and opening of the fraction collector 14 to optimize the collection of component samples.

In the setup process described below the fraction collector 14 can be timed to begin collection before a peak reaches it and to stop collecting before the peak has passed completely. The waste detector 16 senses the portion of the peak that was not collected. Detection of a signal exceeding a predetermined threshold on the waste detector chromatogram indicates the point on the peak where the fraction collector stopped collecting. The optimum fraction collector delay time can be found by comparing the trace to a reference chromatogram obtained by the waste stream detector after allowing a peak to pass uncollected by the fraction collector.

The setup process described here is one way the signature of the waste stream detector can be used to establish the fraction collector delay time, $t_{delay}$. As a first step a peak detected by the triggering detector at time t=0 is allowed to flow to the waste stream detector without opening the fraction collector. Detection of the peak by the waste stream detector at time $t_1$ establishes the closed system flow time. From the length and internal diameter of connecting tubing, estimate the system volume between triggering detector 12 and fraction collector 14 ($V_1$) and between the fraction collector and waste stream detector 16 ($V_2$). Then the time for a peak to reach the fraction collector from the triggering detector can be estimated as $$t_{est}=t_1 \cdot V_1/(V_1+V_2)$$

Make a second injection with the fraction collector delay time set to $t_{setup}=t_{est}-\Delta t_{fc}/2$ where $\Delta t_{fc}$ is the time that the fraction collector remains open, set initially to the width of the eluting peak as measured by the triggering detector. Setting the fraction collector delay time $t_{delay}$ to $t_{setup}$ will cause the fraction collector to start collecting before the peak reaches it, diverting mobile phase into the collection vial, plus the leading portion of the peak. The waste stream detector will subsequently show a response for the trailing portion of the peak not collected. The onset of this response at $t_2$ allows $t_{error}$ to be calculated. $t_{error}$ is the amount by which $t_{setup}$ must be increased to give a fraction collector delay time $t_{delay}$ which will collect the peaks correctly.

$$t_{error}=\Delta t_{fc}-(t_2-t_1)$$

$$t_{delay}=t_{setup}+t_{error}$$

In an illustrative embodiment, the triggering detector 12 comprises a tunable UV detector such as a Model 2487 or a Model 2996 photodiode array detector available from Waters Corp., Milford, Mass. A UV detector such as a Waters Model 2487 detector is suitable for use as a waste stream detector 16. In another illustrative embodiment, the triggering detector 12 and the waste stream detector 16 can be implemented using two analytical channels of a single instrument. For example, two channels on a parallel UV detector such as Waters Model 2488 4 or 8 channel UV detector, or two channels on a Micromass MUX Mass Spectrometer from Waters Corporation can be used as the triggering detector and waste stream detector according to the present invention.

In an illustrative embodiment of the invention, the fraction collector delay timer 15 is a data system including a computer having data acquisition and control functionality operatively connected to the triggering detector, fraction collector and waste stream detector. Suitable software for use in a data system to implement the control timer 15 according to illustrative embodiments of the invention includes Empower software from Waters Corporation of Milford, Mass., or MassLynx software available from the Micromass division of Waters Corporation.

The shape of a chromatographic peak at the waste stream detector is analyzed to determine whether the fraction collector 14 was opened and closed at appropriate times for collecting the desired peak. Such analysis of the waste stream peak in relation to the collected sample can be implemented via mathematical functions, as will be appreciated by those skilled in the art, modeling the operations as described in greater detail hereinafter.

Figure 3:
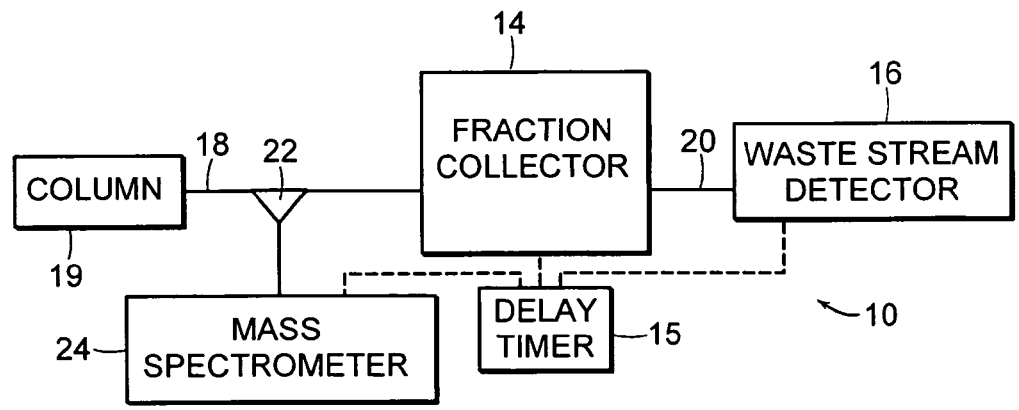
FIG. 3 is a diagrammatic representation of a system flow path including a mass spectrometer and a waste stream detector according to an illustrative embodiment of the present invention.

Turning now to FIG. 3, a system flow path 10 of another illustrative embodiment is described wherein an eluent stream 18 flows from a liquid chromatography column 19 to a stream splitter 22 which directs part of the eluent stream to a destructive detector such as a mass spectrometer 24. The remainder of the eluent stream continues to a fraction collector 14 and then on to a waste stream 20 having a waste stream detector 16 disposed therein. The embodiment illustrated in FIG. 3 replaces the function of the triggering detector 12 with the mass spectrometer 24 wherein the mass spectrometer 24 triggers the fraction collector delay timer upon recognition by the mass spectrometer of a leading edge or threshold level of a desired chromatographic peak.

The presence of the stream splitter 22 in the embodiment of FIG. 3 influences the flow rate of the eluent stream 18 downstream of the splitter and to the mass spectrometer, thereby requiring a different delay time than that required for the system flow path of the embodiment illustrated in FIG. 2. Nonetheless, calibration of a fraction collector actuation time can be implemented in the embodiment of FIG. 3 according to the method of the present invention as described herein wherein the delay time is determined to compensate for the effect of additional path sections in the system flow path 10. Flow rates are more susceptible to change when split flows are involved. The automatic checking and fine-tuning of timing calibration made possible by the present invention is particularly valuable.

Calibration of the fraction collector timing and confirmation of sample collection by the fraction collector using chromatograms output from the waste stream detector is described with reference to FIGS. 4(a)-4(g). Seven illustrative sets of chromatograms are shown corresponding to seven different controller delay conditions. The columns in FIGS. 4(a) to 4(g) represent time increments wherein a peak under consideration (diagrammed as a triangle) transits the triggering detector during the time period represented in the first column 81; the peak under consideration transits the fraction collector during the time period represented by the second column 83; and the peak under consideration transits the waste detector during the time period represented by the third column 85. It should be noted that no chromatogram is actually acquired as the peak transits the fraction collector as indicated in the second column 83. Rather, the second column 83 illustrates the shape of the peak under consideration that would be detected by a hypothetical optical detector in the fraction collector as the peak transits the fraction collector.

The first controller delay condition as represented in FIG. 4(a) occurs when the fraction collector is not triggered at all. This occurs, for example, when an experiment is performed to establish the time $t_1$ for a peak to transit from the triggering detector to the waste detector when the fraction collector is closed. For the purpose of this discussion, all times are referenced to t=0 when the triggering detector detects the leading edge of a peak. The leading edge 80 of a peak 82 is detected at the triggering detector and starts the delay timer at time t=0. The leading edge 80' of a peak 82' arrives at the fraction collector at time $t_{delay}$ (wherein $t_{delay}$ is not yet established). Since no signal is present to open the fraction collector, the entire peak 82" continues in the waste stream and its leading edge 80" is detected by the waste stream detector to establish $t_1$. The chromatogram for the peak 82 detected by the triggering detector at t=0 is substantially the same as the chromatogram for the peak 82" obtained from the waste stream detector at $t_1$ because no fraction is collected.

FIG. 4(b) illustrates a controller delay condition which causes the fraction collector to open and close before the peak reaches it. A mobile phase portion of the eluent stream without the desired components is diverted into collection vessel ahead of the peak. Therefore, the chromatogram signals 86' and 86" are the same as 82' and 82". The chromatogram signals 86' and 86" do not provide delay timing information. A fraction collector timing signal 88 has a leading edge 89 corresponding to a fraction collector open signal $t_{setup}$ and a trailing edge 90 corresponding to a fraction collector close signal. The period during which the fraction collector is open ($\Delta t_{fc}$) is represented by the width 92 of the timing signal 88.

FIG. 4(c) represents chromatograms resulting from a timing signal 96 which occurs earlier than the optimal time for opening and closing the fraction collector but late enough to cause the fraction collector to collect the leading part 98 of a peak 94'. This provides information needed to compute the appropriate delay time. The fraction collector opens at time $t_{setup}$ 97 which occurs before any part of the peak 94 reaches the fraction collector. Mobile phase ahead of the peak and the leading part 98 of the peak 94' is collected before the fraction collector closes. The fraction collector closes at time $t_{setup}+\Delta t_{fc}$ 100. The substantial part 94" of the peak goes to the waste stream.

To optimally collect the peak, the fraction collector should have opened upon arrival at the fraction collector of the leading edge threshold of peak 94'. The event in the waste stream detector chromatogram due to the fraction collector closing is at time $t_2$. Consequently, the waste stream detector chromatogram 94" shows that the fraction collector actually closed at time $t_2-t_1$ 95 after arrival of the peak leading edge threshold at the fraction collector. The error in the delay time is therefore $t_{error}=\Delta t_{fc}-(t_2-t_1)$. The optimal time to trigger the fraction collector is $t_{delay}=t_{setup}+t_{error}=t_{setup}+\Delta t_{fc}-(t_2-t_1)$.

The waste stream detector signal shown in 4(d) occurs when the fraction collector was opened at the substantially optimal time and confirms that the peak was actually collected. The leading edge 104 of the fraction collector timing signal 106 substantially corresponds to the arrival of the leading edge 108 of the desired peak 110' at the fraction collector. The trailing edge 112 of the fraction collector timing signal 106 substantially corresponds to the passage of the trailing edge 114 of the desired peak. The leading edge of the peak passes the fraction collector before collection begins and is frozen in the waste stream as the fraction collection proceeds. When the fraction collector closes (collection is completed), the trailing remnant of the peak is pushed in contact with the leading remnant. Together they flow to the waste stream detector. Only a small residual volume 116 of a peak is indicated on the waste stream chromatogram because the bulk of the fraction is collected.

FIG. 4(e) represents chromatograms resulting from a timing signal 118 which occurs later than the optimal time for opening and closing the fraction collector but early enough to cause the fraction collector to collect the trailing part 120 of a peak 122'. The fraction collector opens at time $t_{setup}$ 124 which occurs after the leading part 126 of the peak 122' has transited the fraction collector. The leading portion of the peak is frozen in the waste line ahead of the waste stream detector. The trailing part 120 of the peak 122' is collected and the fraction collector closes after a period $\Delta t_{fc}$. After a delay of $\Delta t_{fc}$ the leading part 126' of the peak flows to the waste stream where it is detected by the waste stream detector. The event in the waste stream detector chromatogram due to the fraction collector closing is at $t_1$. The timing error can be calculated according to the equation $t_{error}=t_2-(t_1+\Delta t_{fc})$. The late operation of the fraction collector can be adjusted as described herein according to the equation $t_{delay}=t_{setup}+t_{error}$ or equivalently $t_{delay}=t_{setup}+\Delta t_{fc}-(t_2-t_1)$. Note that $t_{error}$ in this case is negative.

In the illustrative embodiments of FIGS. 4(c) and 4(e) the fraction collector event occurs at time $t_2$ in the waste stream chromatogram. When the fraction collector opens early, FIG. 4(c), the event is at the start of the remnant peak and when the fraction collector opens late, the event is at the end of the remnant peak. The delay of the remnant peak by the fraction collector open time, $\Delta t_{fc}$, in FIG. 4(e) distinguishes the two cases. It should be noted that retardation and advancement of the fraction collector timing is measured with respect to detection of a peak in the triggering detector which is used to initiate the delay timer to open the fraction collector.

In FIG. 4(f) it can be seen that the fraction collector timing signal 130 opens the fraction collector after a peak 134' has passed. The flow in the waste stream stops when the fraction collector is open so the peak 134" is "frozen" in the waste stream during that period. Accordingly, when a peak 134" in the waste stream is delayed by a period corresponding to $\Delta t_{fc}$, it can be inferred that the timing signal 130 occurred after the entire peak 134" had passed the fraction collector. Advancement of the timing signal is necessary but the magnitude of $t_{error}$ can not be inferred from the waste stream chromatogram when the entire peak is missed by the fraction collector.

In FIG. 4(g) the fraction collector open signal $T_{FC}$ 136 occurs after a peak has entered the waste stream detector. Since the waste stream does not flow while the fraction collection is open, absorbance in the waste stream detector is frozen for a time $\Delta t_{fc}$ 140 after which the remaining part 142 of the peak passes the waste stream detector. As in FIG. 4(f) it can be inferred that the fraction collector opened too late, and none of the peak was collected. The correct delay time can not be determined from this chromatogram.

Although, band spreading or broadening of the peak often occurs as an eluent stream flows between the triggering detector and the waste stream detector, the timing differences used above recorded at the waste stream detector are not generally affected.

Figure 4:
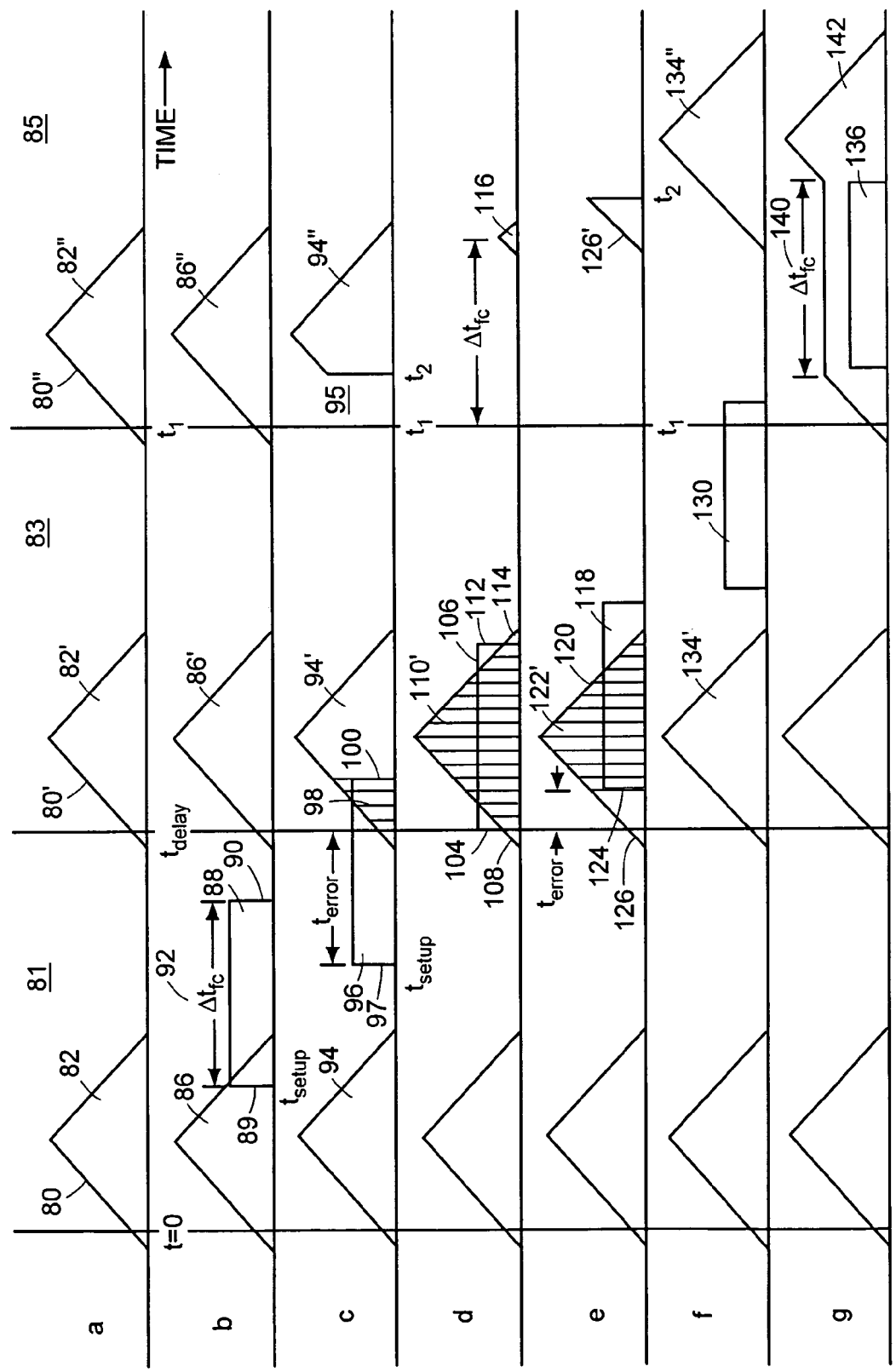
FIGS. 4(a)–4(g) are timing diagrams illustrating the shape of remnant peaks detected in the waste stream relative to the actuation timing of a fraction collector.

As can occur, the peaks in FIG. 4 may be wider than shown and peaks at the triggering detector, fraction collector and waste stream detector overlap in time. This does not affect the ability to compute $t_{delay}$ from the waste stream detector chromatogram as described above.

Actual examples of chromatograms using two UV absorbance detectors are shown in FIGS. 5–8. They illustrate the cases described with the aid of the diagrams in FIG. 4. A diode array detector Waters Model 2996 is used for the triggering detector and a Waters Model 2487 UV detector is used for the waste stream detector. Both detectors measured absorbance at 254 nm. Note that the peak has an unresolved minor component in its tail and the upstream peak (FIG. 5a) has broadened significantly before reaching the waste stream detector (FIG. 5b). These factors do not interfere with the ability of the described method to compute fraction collector delay time from the waste stream detector chromatogram.

Figure 5B:
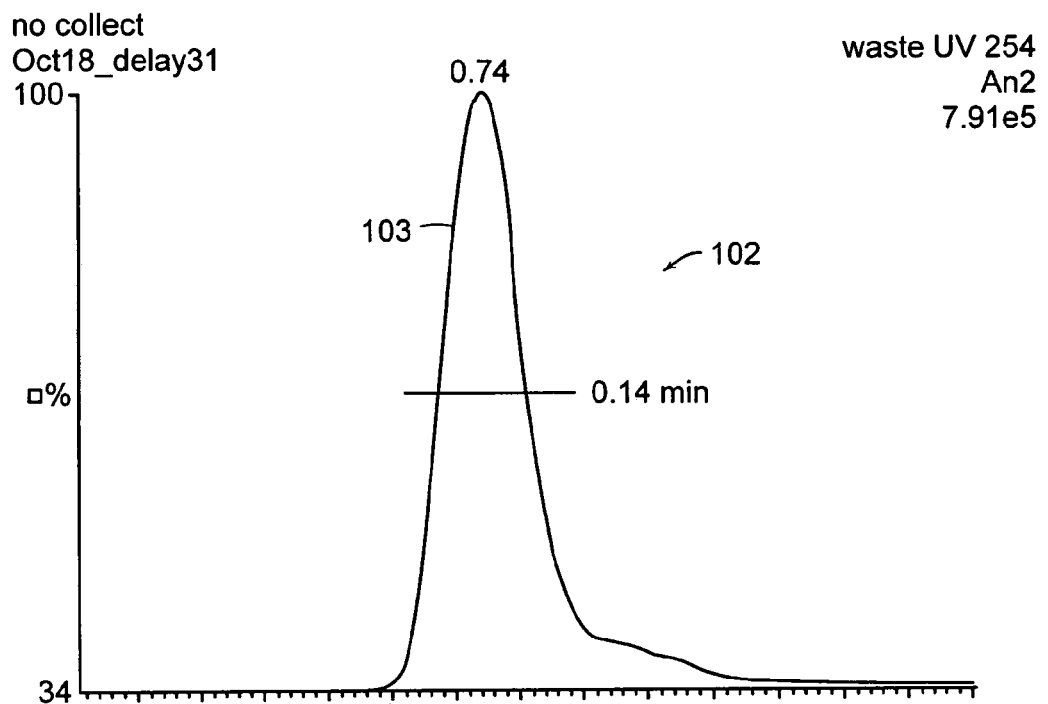
FIG. 5 is a chromatogram of an exemplary peak detected by waste stream detector juxtaposed to a chromatograph of the same exemplary peak detected by a triggering detector.
Figure 5A:
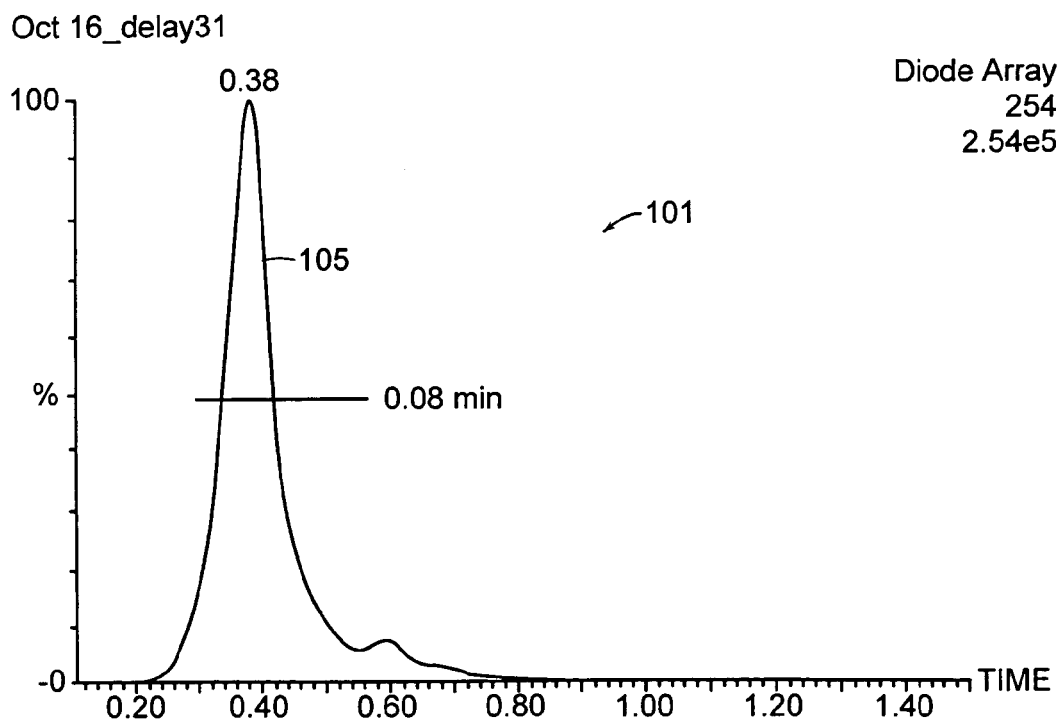

The fraction collector was triggered at steadily increasing delay times from the threshold detection of the triggering detector. The delay time clock is triggered to start (t=0) as the threshold of the peak is detected by the triggering detector. All timing information to correct the fraction collector delay time for optimal collection then comes from observation of the waste stream detector signature. (Note: the timing marks on FIGS. 5–8 start at an arbitrary point before the peak reaches the triggering detector) FIG. 5b shows the waste stream signature when the fraction collector does not open, similar to the case shown in FIG. 4a. Some band broadening is evident in the waste stream signature, which affects all waste stream chromatograms to the same extent.

An example will be described wherein the invention was embodied with the triggering detector 12 was a UV-visible photodiode array detector by Waters Corporation, Model No. 2996. The waste stream detector 16 was a dual wavelength tunable wavelength UV-visible detector by Waters Corporation, Model No. 2487. The triggering detector 12 and the waste stream detector 16 were both configured to detect peaks absorbing at a wavelength of 254 nanometers. Referring now to FIG. 5, a waste stream chromatogram 102 and an upstream chromatogram 101 as detected by the triggering detector 12 and waste stream detector 16 of the present example are represented. The substantial similarity between the waste stream peak 103 and the upstream peak 105 is consistent with no part of the peak being collected by the fraction collector, which during this run did not open. A similar result would have been obtained had the fraction collector opened, but too early to collect any portion of the peak. Compare with FIGS. 4(a) and 4(b).

Figure 6:
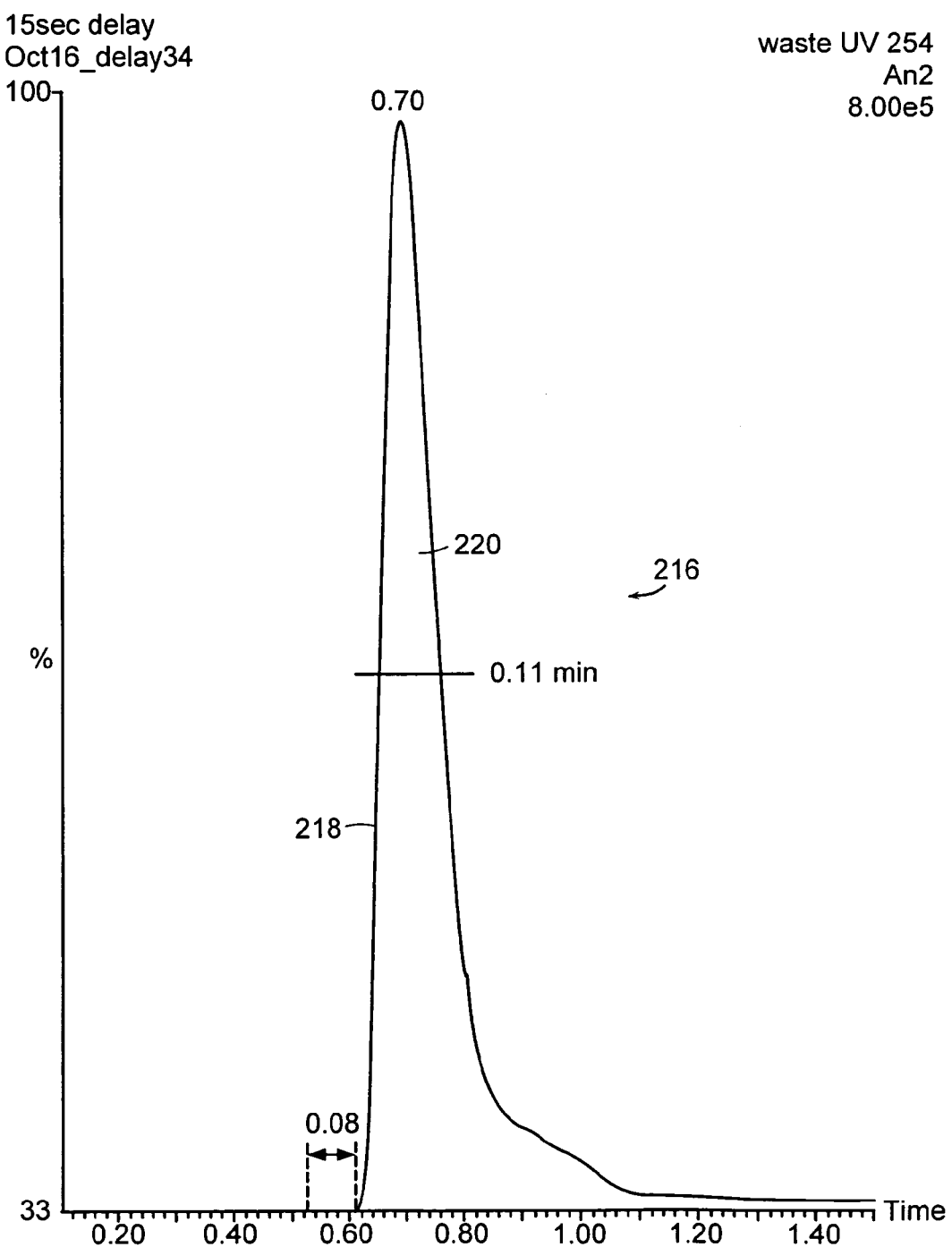
FIG. 6 is a chromatogram of an exemplary peak detected in the waste stream after a fraction collector is actuated with too short a delay time.

FIG. 6 represents a waste stream chromatogram 216 rendered by the apparatus of the present example wherein the time delay between detection of a peak at the triggering detector and opening of the fraction collector is configured to 15 seconds ($t_{setup}$). In the present example, the fraction collector can be seen to have closed 0.08 minutes (approximately 5 seconds) after the peak arrived at the fraction collector. The vertical leading edge 218 in the waste stream peak 220 indicates an early actuation and early closing of the fraction collector. (See also the analogous illustration in FIG. 4(c)). The leading portion of the peak 220 was collected by the fraction collector as evidenced by its absence from the waste stream detector chromatogram. The timing delay error ($t_{error}$) is calculated as $\Delta t_{fc}$ minus 5 seconds. $t_{error}$ can be added to $t_{setup}$, the fraction collector delay time used in FIG. 6, to calibrate the desired fraction collector timing.

Figure 7:
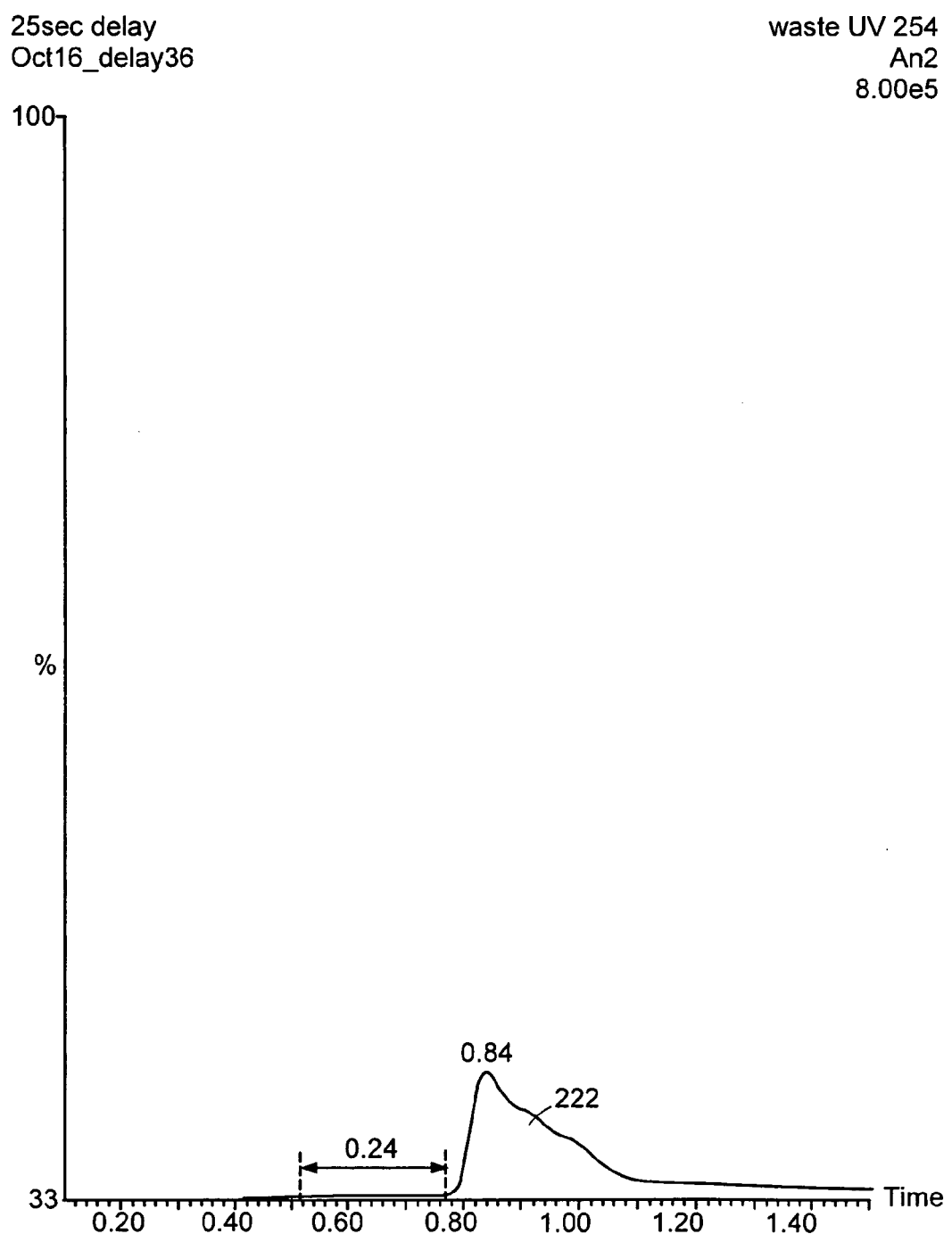
FIG. 7 is a chromatogram of an exemplary peak detected in the waste stream after a fraction collector was actuated with near optimal timing.

Referring now to FIG. 7 the apparatus of the example was configured to open the fraction collector 25 seconds after a peak is detected at the triggering detector ($t_{setup}$=25 sec.). Most of the peak is collected by the fraction collector indicating substantially optimal calibration. A small peak 222 detected in the waste stream represents the trailing edge of the main peak. In some embodiments of the invention, it may be desirable to avoid collecting the trailing edge of the main peak, because the trailing portion of a peak may contain contamination. The fraction collector timing in this case allowed the trailing edge of the peak to pass to the waste stream.

Figure 8:
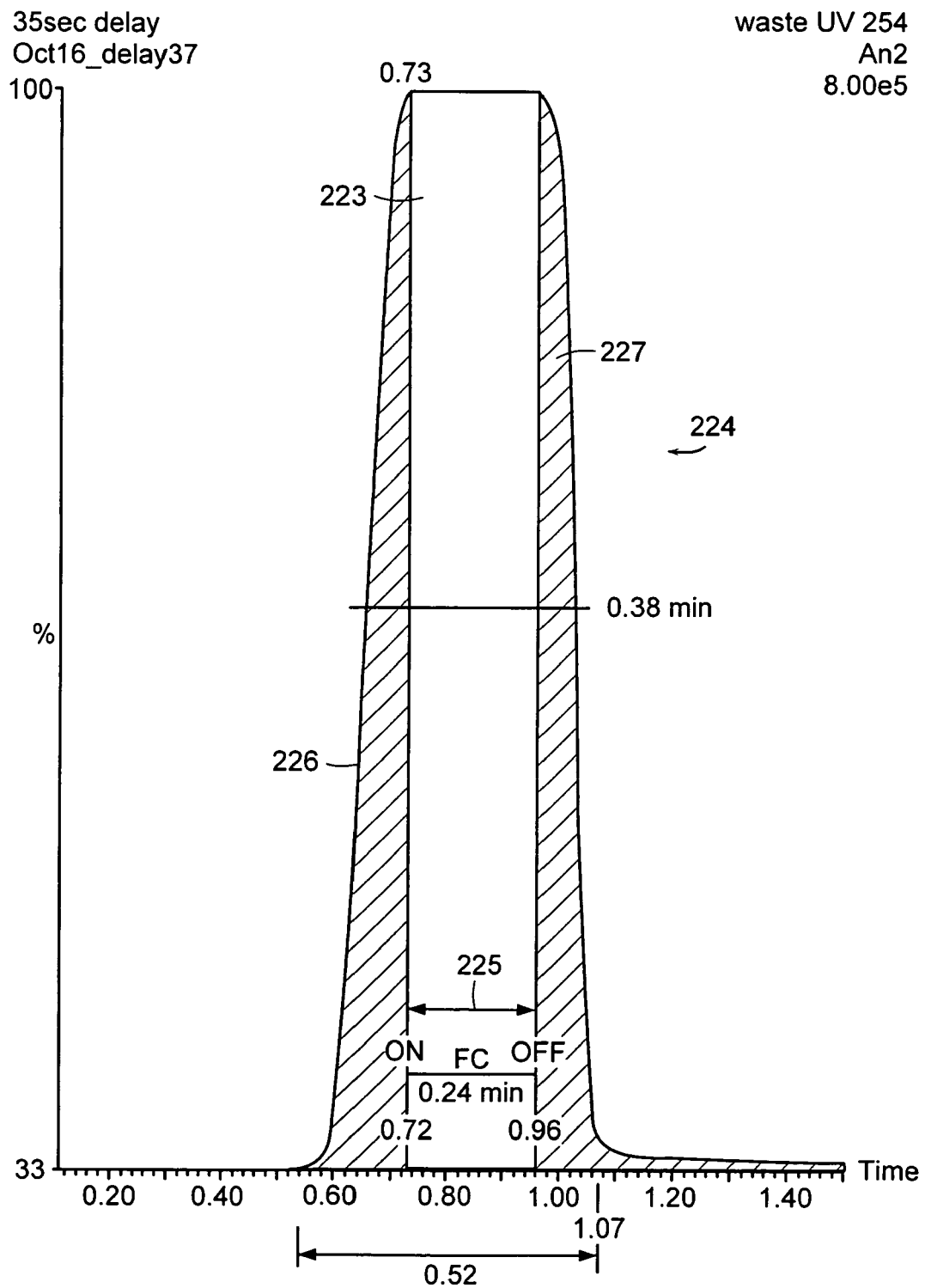
FIG. 8 is a chromatogram of an exemplary peak detected in the waste stream after a fraction collector was open with too long a delay time.

FIG. 8 illustrates a chromatogram 224 rendered by the waste stream detector of the present example wherein the delay time is set to 35 seconds. Here, the leading edge 226 reaches the waste stream detector before the fraction collector is opened. (See also, the analogous illustration in FIG. 4(g)). UV absorbance by the waste stream detector is frozen during the time that the fraction collector is open ($\Delta t_{fc}$) 225. The remainder 227 of the peak 223 then flows into the waste stream where it is detected by the waste stream detector.

Figure 9:
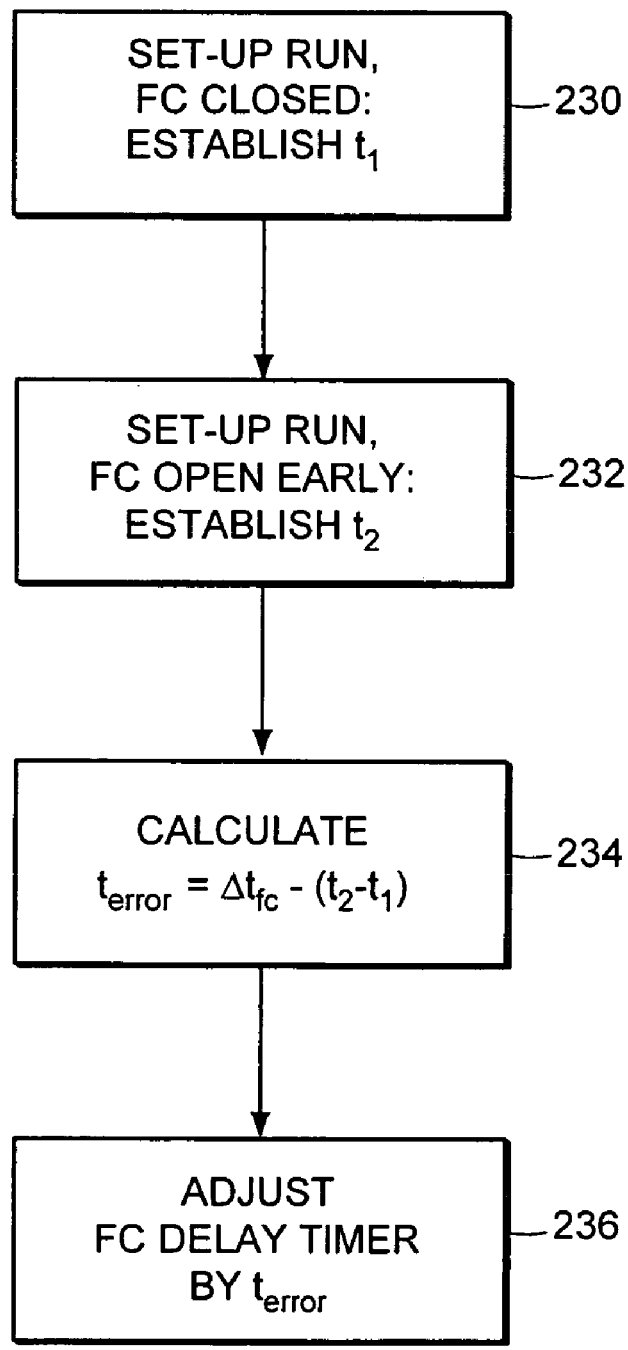
FIG. 9 is a process flow diagram of a calibration method according to an illustrative embodiment of the invention.

Referring now to FIG. 9, a system flow diagram illustrates the method of calibrating a fraction collector according to an illustrative embodiment of the invention. A first set-up run is performed 230 wherein a peak is injected upstream of the triggering detector. The peak is allowed to flow from the triggering detector to the waste stream detector without triggering the fraction collector. Times of detection of the peak threshold by the triggering detector t=0 and the waste stream detector $t_1$ is noted. This provides information about the flow time between the triggering detector and the waste stream detector. A second set-up run is then performed 232 wherein the fraction collector is intentionally triggered early or late at time $t_{setup}$ such that the fraction closing or opening event is observed in the waste stream detector signature. The time of this event in the waste stream signature is $t_2$. This combined with $t_1$ provides information from which to calculate $t_{error}$ 234. Finally $t_{error}$ is added 236 to $t_{setup}$ to compute $t_{delay}$ to calibrate the fraction collector and thereby facilitate collection of substantially all of the peak. (See also FIG. 4d). The value of $t_{error}$ is positive when the fraction collector opens early, but negative when the fraction collector opens late.

Although the illustrative embodiments are described herein primarily with respect to a fraction collector timing control signal calibrated with reference to output from a UV type waste stream detector in combination with an upstream UV detector to provide peak identification and triggering, persons having ordinary skill in the art should appreciate that various optical detectors such as refractive index detectors or fluorescence detectors can be used to detect peaks in the waste stream (or upstream) and provide calibration information according to the method and apparatus of the present invention. Persons skilled in the art should appreciate that destructive detectors such as mass spectrometers, evaporative light scattering detectors or nitrogen detectors can also be used to detect peaks in the waste stream (or upstream using a splitter) and provide calibration information for fraction timing according to the method and apparatus of the present invention. Mixed detectors are also feasible, such as a mass spectrometer to identify the fraction upstream and start the delay timer, in combination with a UV detector in the waste stream.

Although embodiments of the present invention are described with respect to eluent streams from a liquid chromatography column, persons having ordinary skill in the art should appreciate that the method of the present invention can be used to calibrate timed collection devices in various different fluid analysis systems.

Although embodiments of the invention are described herein which measure timing signals according to the detection of a threshold, or lift-off portion of a detected peak, persons having ordinary skill in the art should appreciate that other portions of the peak, such as the top point of a detected peak, can also be used to measure timing signals and perform fraction collector calibration according to the invention.

Although the invention is described herein in terms of detecting a single component in an eluent stream, persons skilled in the art should appreciate that the apparatus of the present invention could also be programmed to recognize peak characteristics of multiple components in an eluent stream and trigger the fraction collector to collect the multiple components.

Although the invention is described herein in terms of calibrating the timing of a fraction collector and confirming the collection of components, persons skilled in the art should appreciate that characteristics of signals detected by a waste stream detector according to the invention can be used for a number of other purposes. For example, various qualities of collected samples can be inferred from waste stream chromatograms. Embodiments of the invention can be programmed to shut down a separation run or trigger an alarm condition if the quality of collected samples falls outside of predetermined limits. The waste stream detector may also be used to direct the collection of components, not collected in the primary fraction collector, to a waste stream fraction collector for possible further purification and tests.

Although the invention is described herein in terms of measuring time differences between detection of components in an eluent stream, persons skilled in the art should appreciate that flow volumes can also be measured and used to calibrate fraction collector timing signals without departing from the spirit and scope of the present invention.

Although the invention is described hereinbefore with respect to illustrative embodiments thereof, persons having ordinary skill in the art should appreciate that the foregoing and various other changes, omissions and additions in the form and detail thereof may be made without departing from the spirit and scope of the invention.

What is claimed is:

1. A method of calibrating fraction collector timing in a fluid stream comprising:
   detecting a desired component in said fluid stream prior to said component arriving at a fraction collector;
   initiating a fraction collector delay timer upon detection of said desired component;
   triggering said fraction collector to open when a delay time elapses after initiating said fraction collector delay timer; and
   detecting said desired component in a waste stream from said fraction collector, wherein a signature of fraction collector actuation, observed by said waste stream detector, enables said delay time to be established.

2. The method according to claim 1 further comprising:
   calculating a timing error of said first pre-determined delay time according to time of detection of said desired component in said waste stream; and
   adjusting said delay time to eliminate said timing error.

3. The method according to claim 2 wherein said timing error is calculated by:
   comparing the time of detection of a said desired component in said waste stream when a portion of said desired component is collected by said fraction collector with the expected time of detection of said component in said waste stream.

4. The method according to claim 3 wherein said expected time of detection is determined by measuring the time for said desired component to flow from a triggering detector to a waste stream detector when said fraction collector is not triggered.

5. The method according to claim 2 wherein said calculating, adjusting and triggering is performed automatically by a data system in communication with a triggering detector, a waste stream detector and said fraction collector.

6. The method according to claim 1 wherein said fluid stream is an eluent stream flowing from a liquid chromatography column.

7. The method according to claim 1 wherein said detecting prior to said desired component arriving to said fraction collector is performed using a UV detector.

8. The method according to claim 1 wherein said detecting prior to said desired component arriving to said fraction collector is performed using a mass spectrometer in a separate branch of said eluent stream.

9. The method according to claim 1 wherein said detecting of said desired component in said waste stream is performed using a detector selected from the group consisting of a UV detector and a mass spectrometer.

10. A method for calibrating fraction collector timing in a liquid chromatography eluent stream comprising:
    providing a fraction collector in said eluent stream;
    providing a triggering detector in said eluent stream wherein said triggering detector is capable of detecting a desired component before arrival of said desired component at said fraction collector;
    providing a waste stream detector downstream of said fraction collector in said eluent stream;
    establishing a closed system waste stream detection time ($t_1$) by detecting a desired component with said triggering detector, holding said fraction collector closed and measuring the elapsed time before said desired component is detected in said waste stream detector;

establishing a delay error ($t_{error}$) by:
  estimating a fraction collector delay time;
  operating said fraction collector while said peak is still passing said fraction collector;
  detecting an edge ($t_2$) of a remnant of said desired component with said waste stream detector and measuring the arrival time of said edge;
  computing said delay error and correcting said estimated fraction collector delay time to determine the desired fraction collector delay time.

11. The method according to claim 10 further comprising:

providing a data system in communication with said fraction collector, said triggering detector and said waste stream detector;

receiving signals with data system from said triggering detector and said waste stream detector upon detection of said desired component by each of said detectors;

automatically computing $t_{error}$ and calibrating said fraction collector delay time upon subsequent detections of said desired component.

* * * * *